(12) United States Patent
Kissa-Marin et al.

(10) Patent No.: US 9,588,107 B2
(45) Date of Patent: Mar. 7, 2017

(54) TOOL FOR STUDYING ENDOTHELIAL HAEMATOPOIETIC TRANSITION (EHT) AND EPITHELIAL-MESENCHYMAL TRANSITION (EMT) ASSOCIATED EVENTS

(75) Inventors: Karima Kissa-Marin, Montpellier (FR); Philippe Herbomel, Paris (FR)

(73) Assignee: AZELEAD, Montpellier (FR)

( * ) Notice: Subject to any disclaimer, the term of this patent is extended or adjusted under 35 U.S.C. 154(b) by 0 days.

(21) Appl. No.: 13/383,973

(22) PCT Filed: Jul. 14, 2010

(86) PCT No.: PCT/IB2010/002156
§ 371 (c)(1),
(2), (4) Date: Mar. 22, 2012

(87) PCT Pub. No.: WO2011/007259
PCT Pub. Date: Jan. 20, 2011

(65) Prior Publication Data
US 2012/0180145 A1    Jul. 12, 2012

(51) Int. Cl.
*G01N 33/00* (2006.01)
*A01K 67/027* (2006.01)
*G01N 33/50* (2006.01)

(52) U.S. Cl.
CPC ............................... *G01N 33/5088* (2013.01)

(58) Field of Classification Search
CPC .................................................. G01N 33/5088
See application file for complete search history.

(56) References Cited

U.S. PATENT DOCUMENTS

2006/0018833 A1\* 1/2006 Murphy et al. ............... 424/9.2

FOREIGN PATENT DOCUMENTS

WO    2008/150498    12/2008

OTHER PUBLICATIONS

Kissa, Live Imaging of Emerging Hematopoietic Stem Cells and Early Thymus Colonization, Blood, 111, pp. 1147-1156, 2008.
Ghosh, Nontoxic Chemical Interdiction of the Epithelial-to-Mesenchymal Transition by Targeting Cap-Dependent Translation, ACS Chemical Biology, 4, pp. 367-377, 2009.
Kovacic, Resident Vascular Progenitor Cells: An Emerging Role for Non-Terminally Differentiated Vessel-Resident Cells in Vascular Biology, Stem Cell Research, 2, pp. 2-15, 2009.
Zovein, Fate Trancing Reveals the Endothelial Origin of Hematopoietic Stem Cell, Cell Stem Cell, 3, pp. 625-636, 2008.
Bertrand, Hematopoietic Cell Development in the Zebrafish Embryo, Current Opinion in Hematology, 16, pp. 243-248, 2009.
Kissa, Blood Stem Cells Emerge from Aortic Endothelium by a Novel Type of Cell Transition, Nature, 464, pp. 112-116, 2010.
Bertrand, Haematopoietic Stem Cells Derive Directly from Aortic Endothelium During Development, Nature, 464, pp. 108-112, 2010.
Cumano, Ontogeny of the Hematopoietic System, Annual Review of Immunology, 25, pp. 475-485, 2007.
International Search Report for PCT/IB2010/002156.

\* cited by examiner

*Primary Examiner* — Doug Schultz
(74) *Attorney, Agent, or Firm* — Young & Thompson (57) ABSTRACT

The present invention relates to the field of endothelial haematopoietic transition (EHT) and epithelial-mesenchymal transition (EMT) and more particularly relates to the use of fish embryo or larva as a model for the study of EHT and EMT.

2 Claims, 7 Drawing Sheets

TOOL FOR STUDYING ENDOTHELIAL HAEMATOPOIETIC TRANSITION (EHT) AND EPITHELIAL-MESENCHYMAL TRANSITION (EMT) ASSOCIATED EVENTS

RELATED APPLICATIONS

The present application is a U.S. National Phase Application of International Application No. PCT/IB2010/002156 (filed Jul. 14, 2010) which claims priority to Canadian Application No. 2,672,014 (filed Jul. 14, 2009) which are hereby incorporated by reference in their entirety.

FIELD OF THE INVENTION

The present invention relates to the field of endothelial haematopoietic epithelial transition (EHT) and epithelial mesenchymal transition (EMT) and more particularly relates to the use of a fish embryo or larva as a model for the study of EHT and EMT.

BRIEF DESCRIPTION OF THE PRIOR ART

The ontogeny of haematopoietic stem cells (HSCs), which give rise to all blood and immune cells in the body, during embryonic development is still highly debated, especially their possible lineage relationship to vascular endothelial cells[1,2].

The first anatomical site from which cells with long-term HSC potential have been isolated is the aorta-gonad-mesonephros (AGM), more specifically the vicinity of the floor of the dorsal aortic (DA)[3]. But while some authors have presented evidence that HSCs may arise directly from the aortic ventral floor into the dorsal aortic (DA) lumen[4], others support the notion that HSCs first emerge within the underlying mesenchyme[5]. A review of the embryonic origins of human haematopoiesis suggest that haematopoietic clusters within the AGM are pluripotent cells that have diverged from an endothelial-like precursor.[6]

Epithelial to mesenchymal transition (EMT) is a central event in embryonic development as well as in tumour metastasis and progression. EMT is a phenotypic cell transition where, in normal tissue development or in tumour progression and metastasis, the epithelial cells disperse by weakening the cell-cell adhesion system, and show mobile and sometimes invasive cell behaviour as mesenchymal cells. To understand EMT dependent events (e.g. tumour progression and metastasis) and similar events, the mechanism of EMT must be elucidated.

SUMMARY

The present invention provides a new tool for understanding the mechanism of EHT and/or EMT dependent events.

More particularly, an object of the invention concerns the use of a fish embryo or larva as a model for the study of endothelial haematopoietic transition (EHT) or epithelial mesenchymal transition (EMT).

Another object of the invention concerns the use according to the invention, wherein the embryo or larva comprises vascular cells.

Another object of the invention concerns the use according to the invention, wherein the vascular cells consist of arterial cells.

Another object of the invention concerns the use according to the invention, wherein the fish consists of zebrafish or Medaka.

Another object of the invention concerns the use according to the invention, wherein the study of EHT or EMT consists of an in vivo study of EHT.

Another object of the invention concerns the use according to the invention, wherein the study of EHT or EMT consists of an in vitro study of EHT, wherein the embryos or slices thereof have been fixed on fixed tissue.

Another object of the invention concerns the use according to the invention, wherein the embryo or larva consists of a transgenic embryo or larva.

Another object of the invention concerns the use according to the invention, wherein the embryo or larva comprises a marker for vascular cells, HSC cells or endothelial cells.

Another object of the invention concerns the use according to the invention, wherein the marker is associated with a reporter gene.

Another object of the invention concerns the use according to the invention, wherein the reporter gene is green fluorescent protein (GFP) or discosoma red protein (Dsred).

Another object of the invention concerns the use according to the invention, wherein the marker for vascular cells is CD41, runx1 or cmyb.

Another object of the invention concerns the use according to the invention, wherein the endothelial marker is KDR, kdrl, Fli, Fli-1, Lmo2, ephrinB2 or Tie-2.

Another object of the invention concerns the use according to the invention, wherein the transgenic fish or transgenic larva is selected from the group consisting of CD41-GFP zebrafish, KDR-GFP zebrafish, Lmo2-Dsred zebrafish, Lmo2-Dsred/CD41-GFP zebrafish, Tie-2-GFP and Fli1-GFP.

Another object of the invention concerns the use according to the invention, wherein the study of EHT or EMT consists of an inhibitory study of EHT or EMT.

Another object of the invention concerns the use according to the invention, wherein the study of EHT or EMT consists of an inducing study of EHT or EMT.

Another object of the invention concerns a method for screening for a candidate compound that modulates the endothelial haematopoietic transition (EHT) or epithelial-mesenchymal transition (EMT) mechanism, comprising the steps of:
  introducing a candidate compound into a fish embryo or larva according to the invention; and
  evaluating the capacity of said candidate compound to modulate the EHT or EMT mechanism, said modulation being an EHT or an EMT inhibitory effect or an EHT or an EMT inducing effect.

BRIEF DESCRIPTION OF THE FIGURES

a. Global view of a KDR-GFP embryo at 26 hours post fertilization (h.p.f.); GFP fluorescence highlights the whole vasculature; the boxed area was imaged by time-lapse confocal microscopy from 36 h.p.f. to 52 h.p.f. (b-v) at 14 depth z planes (Z1 to Z14) spaced by 2 µm, every 5 min. Time is indicated in hrs and min. from T0=36 h.p.f. (b). White numbers indicate recording time in hours and minutes, aortic cells undergoing delamination or EHT are numbered in red, i.e., in the order in which they delaminate or exit from the DA floor. Cell 10 is not yet visible in b because the whole vasculature and somites are slowly moving rostralwards in this phase of development. Cells 6a, 6b, 9a, 9b are daughters of cells 6 and 9, respectively. Each image is from a single confocal plane, mostly Z10 (b-o); inset in b is from Z4 to show the already exited or delaminated cells 1 and 2; p, Z6, q, Z11, r-v, Z7. Arrows in b show the sense of circulation in the dorsal aortic (DA) and axial vein (AV). Arrowheads in f and l show the thin line evidencing the joining of the left and right (lateral) neighbours of the delaminating or exiting cell, whereas arrowheads in g, h and m, point at their remaining focal attachment sites to rostral and caudal neighbours. A dotted line in s-v shows the trajectory of cell 6b from the sub-aortic space into a small niche within the AV microstroma (arrowhead in r,s), and its disappearance from there (v) as it entered the blood stream. Scale bars, 25 µm (b), 10 µm (c-o), 10 µm (p-v). See also Movie 1 for the complete time-lapse sequence at z10.

a-c, Live KDR-GFP embryos and larvae. a, Three KDR-GFP+ hematopoietic cells beneath the DA, one along the DA floor and two within the reticulated dorsal wall of the axial vein (AV), one of which will soon enter the vein lumen. b, The first HSPCs that seed the caudal hematopoietic tissue (CHT) by 35 h.p.f. (black arrowhead on the video-enhanced DIC image to the left), are KDR-GFP+ (white arrowhead). c, The hematopoietic progenitors that seed the thymus rudiment (t) by 58 h.p.f. are KDR-GFP+; phs, primary head sinus (cephalic vein); oc, otic capsule. d-j, Live [Lmo2-DsRed; CD41-GFP] double transgenic embryos; d-f, A bending, Dsred+ cell of the DA floor already expresses CD41-GFP detectably (d), although less than already emerged HSPCs (blue asterisks); 20 min later (e,f), the joining of its endothelial lateral neighbors is visible (e, black arrowheads in the DIC image), and the next focal plane (f) reveals the cell beginning to round up. Consistently, before the joining (d), circulating erythrocytes in the DA, appearing as red stripes due to the scanning process, still come in contact with the bending cell (d, white arrowhead), whereas they no longer do so after the joining (e). g-j, Progressive rise in CD41-GFP expression in a Lmo2-Dsred+ DA floor cell (white asterisk) as it undergoes delamination; blue asterisks, CD41-GFP+ HSPC, dividing between timepoints i and j. Scale bars, 10 µm (a,b), 50 µm (c), 10 µm (d-f), 25 µm (g-j).

a-i, Time-lapse imaging of GFP fluorescence in a KDR-GFP embryo/larva from 28 h.p.f. to 100 h.p.f. Maximum projection from 18 z-planes spaced by 3 µm, color-coded such that cells change colors as they move from one z-plane to another. a-c. Between 30 and 37 h.p.f., DA diameter expands rapidly, and undergoes cell rearrangements; a white and a yellow arrowhead here follow two DA cells that move respectively from the DA lateral wall (side) and roof of the DA wall to reach its floor before the peak of delamination or EHT events. d-h, Rise, peak then decrease of delamination (or EHT) events (asterisks showing some) correlate with a gradual reduction of the DA diameter, which then remains stable (i). j, The temporal evolution of the DA diameter in this embryo (green solid line), measured every 2 hrs, and its correspondence with panels a-i. The DA diameter in the 18-28 h.p.f. interval (blue dotted line) was measured from another embryo. Scale bar, 25 µm (a-i). The time-lapse sequence from 28 to 60 h.p.f. can also be visualized as Movie 5.

Time-lapse imaging between 29 h.p.f. and 39 h.p.f. of a KDR-GFP embryo injected with an anti-Runx1 morpholino at the one-cell stage. Due to the rostralwards movement of the whole vasculature, cell #3 is not present yet in the imaged field at t=0 (29 h.p.f.), hence the global view of the latter (a) is shown at 37.3 h.p.f. Numbers in red indicate recording time in hours and minutes. The three numbered DA floor cells initiate EHT, but then burst into pieces (arrowheads). Scale bars, 20 µm (a), 10 µm (b-g). The entire time-lapse sequence is also visible as Movie 6. A similar outcome with only rare, abortive EHT events was observed in 4/4 Runx1 morphant embryos subjected to time-lapse confocal analysis.

The figure depicts in transverse and sagittal views the successive steps of the endothelial to haematopoietic transition (EHT) identified in this work by in vivo imaging of zebrafish embryos. DA, dorsal aortic; AV, axial vein.

a, Close-to-sagittal confocal fluorescence section (caudal to the top) of a live KDR-GFP embryo at 52 h.p.f, counterstained with Bodipy TR (red) to reveal the histological context; nc, notochord. Arrows show the sense of circulation in the DA and axial vein (AV). The endothelial DA floor cell marked by an asterisk is then followed through time in longitudinal (b,d,f,h) and transverse (c,e,g,i) section in the transverse plane marked by the double arrow in a. Arrowheads in (c,e,g,i) point at the left and right boundaries of the exiting cell, which end up joined in g; the cell is then no longer part of the aortic wall, but still retains focal contacts with the aortic cells that were its rostral and caudal (i.e. upstream and downstream) neighbors (f). Note that the DA width evolves from 25 µm in (a-c) to 16 µm once the endothelial cell has exited (g,i). Time is indicated in hours and minutes after the onset of the time-lapse recording session. Scale bars, 25 µm (a), 10 µm (b,d,f,h), 25 µm (c,e,g,i). Corresponding, but longer, longitudinal and transverse time-lapse sequences are also shown as Movies 2 and 3.

a-c, Live KDR-GFP embryos and larvae. a, Three KDR-GFP+ haematopoietic cells beneath the DA, one along the DA floor and two within the reticulated dorsal wall of the AV, one of which will soon enter the vein lumen (see also Movie 2). b, The first HSPCs that seed the CHT by 35 h.p.f. (black arrowhead on the video-enhanced DIC image to the left) are KDR-GFP+ (white arrowhead). c, The HSPCs that seed the thymus rudiment (t) by 58 h.p.f. are KDR-GFP+; phs, primary head sinus; oc, otic capsule. d-g, Live CD41-GFP larva injected at the one-cell stage with KDR-dTomato plasmid, imaged at 7 d.p.f.; the kidney (k) area, boxed in d, is shown enlarged in e-g; four of the five dTomato1 cells present in this field (e, arrowheads) are also GFP1 (f, g); g, gallbladder (autofluorescent). h-n, Live (Lmo2-Dsred; CD41-GFP) double transgenic embryos. h-j, A bending, Dsred1 cell of the DA floor already expresses CD41-GFP detectably (h), although less than already emerged HSPCs (blue asterisks); 20 min later (i, j), the joining of its endothelial lateral neighbours is visible (i, black arrowheads), and the next focal plane (j) reveals the cell beginning to round up. Consistently, before the joining (h), circulating erythrocytes in the DA, appearing as red stripes due to the scanning process, still come in contact with the bending cell (h, white arrowhead), whereas they no longer do after the joining (i). k-n, Progressive rise in CD41-GFP expression in a Lmo2-Dsred1 DA floor cell (white asterisk) as it undergoes delamination or EHT; blue asterisks, CD41-GFP+ HSPC, dividing between time points m and n. Scale bars, 10 µm (a, b and h-j), 50 µm (c and e-g), 100 µm (d), 25 µm (k-n).

BRIEF DESCRIPTION OF THE MOVIES

Figure 1:
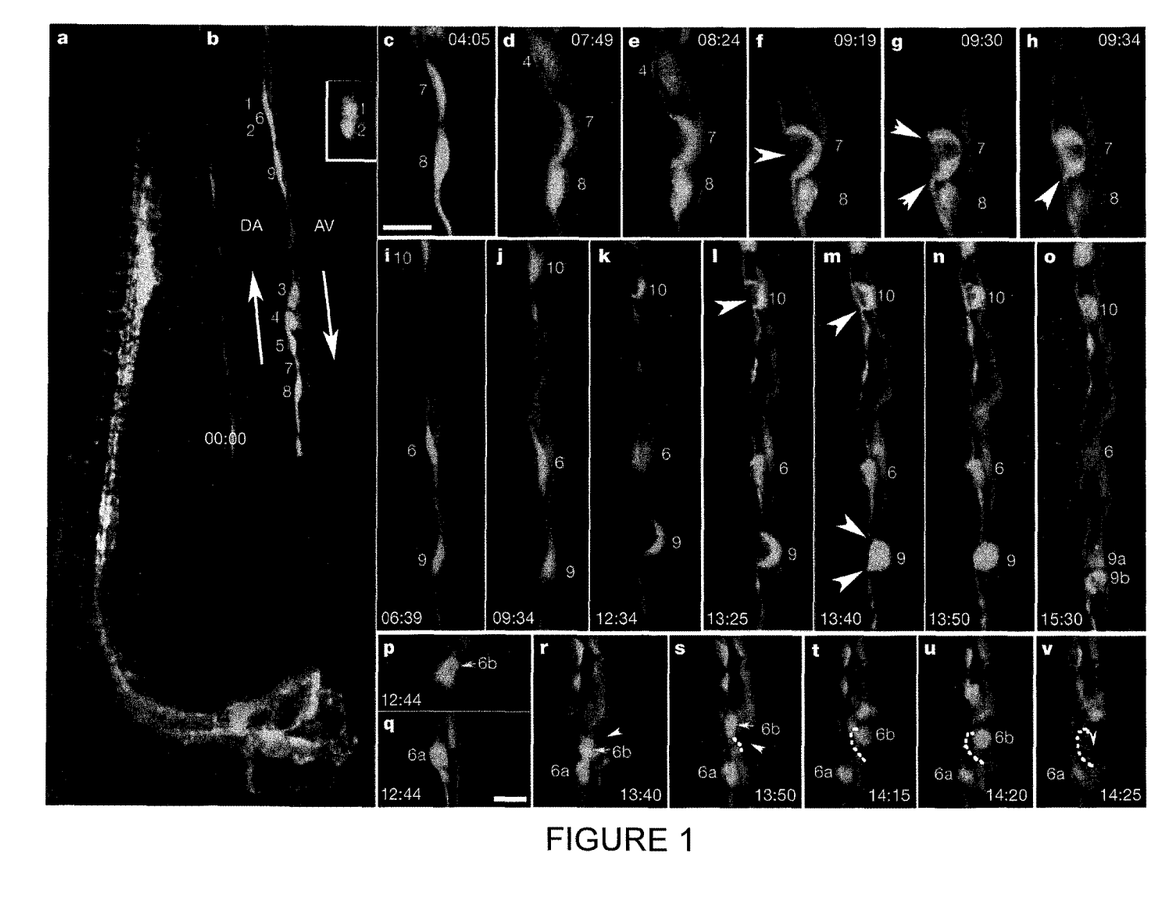
FIG. 1: Endothelial cells from the dorsal aortic floor exit (or delaminate) into the sub-aortic space by a EMT process to become haematopoietic cells.
Figure 5:
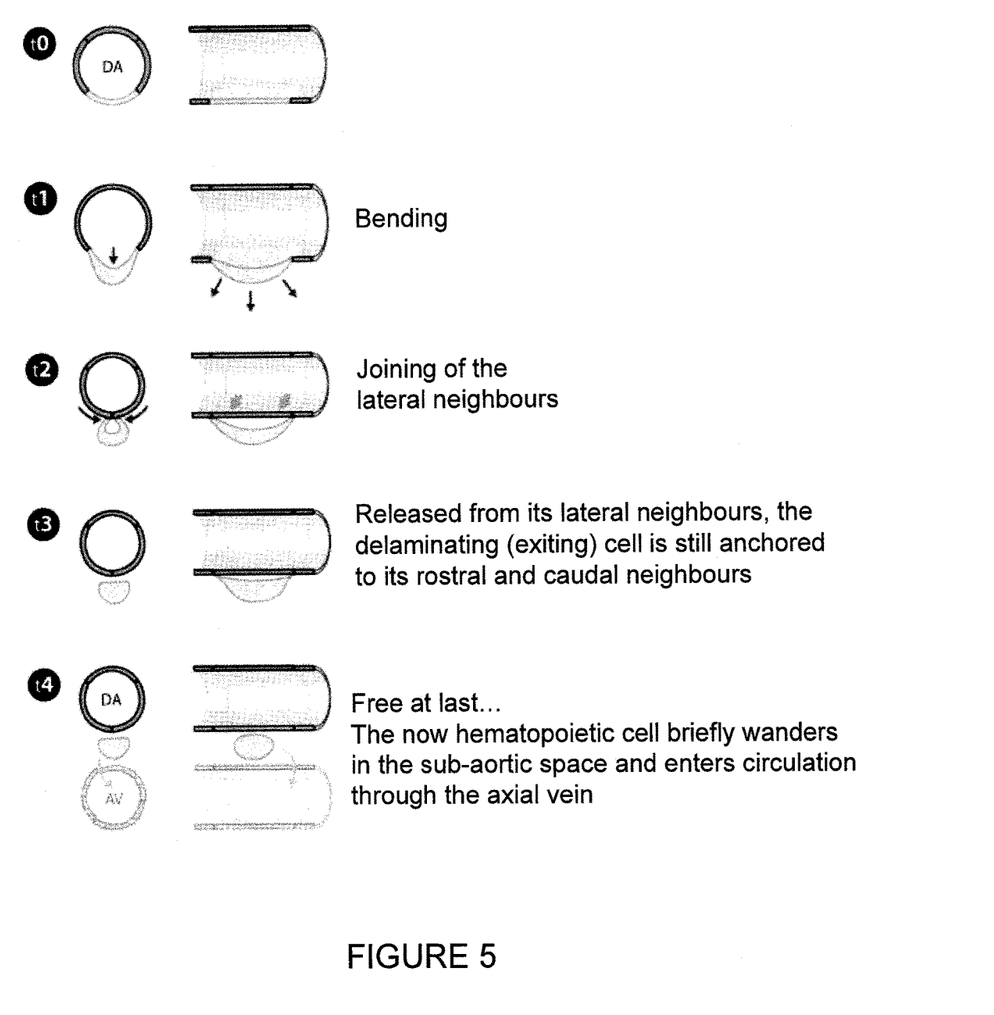
FIG. 5: Endothelial cells from the aortic floor transform into haematopoietic cells in vivo by a new type of cell behaviour.

Movie 1. This movie shows the time-lapse confocal fluorescence imaging of the dorsal aortic (DA)/axial vein (AV) joint in the upper trunk region of a KDR-GFP transgenic zebrafish embryo, from 36 to 52 hrs post fertilization (1 frame/5 min). Endothelial cells from the DA floor are seen to contract, bend, then exit into the sub-aortic space to become haematopoietic cells, according to a stereotyped sequence depicted in FIG. 5, which the inventors have named the endothelial haematopoietic transition (EHT). They then move, may divide, and enter the blood circulation through the axial vein. Past the first image which shows the position of all numbered cells, each cell's number appears in the movie short before the cell initiates the EHT process. Since the embryo is imaged in lateral view, the bending of DA floor cells initiating EHT is best seen for cells whose main axis is close to the sagittal plane (e.g. cells 7, 9). The movie shows only one confocal plane; selected frames are shown in FIG. 1, which also shows images from other z-planes of the same time-lapse confocal series. Time is indicated in hours, minutes, seconds, in the upper right corner of the image.

Figure 6:
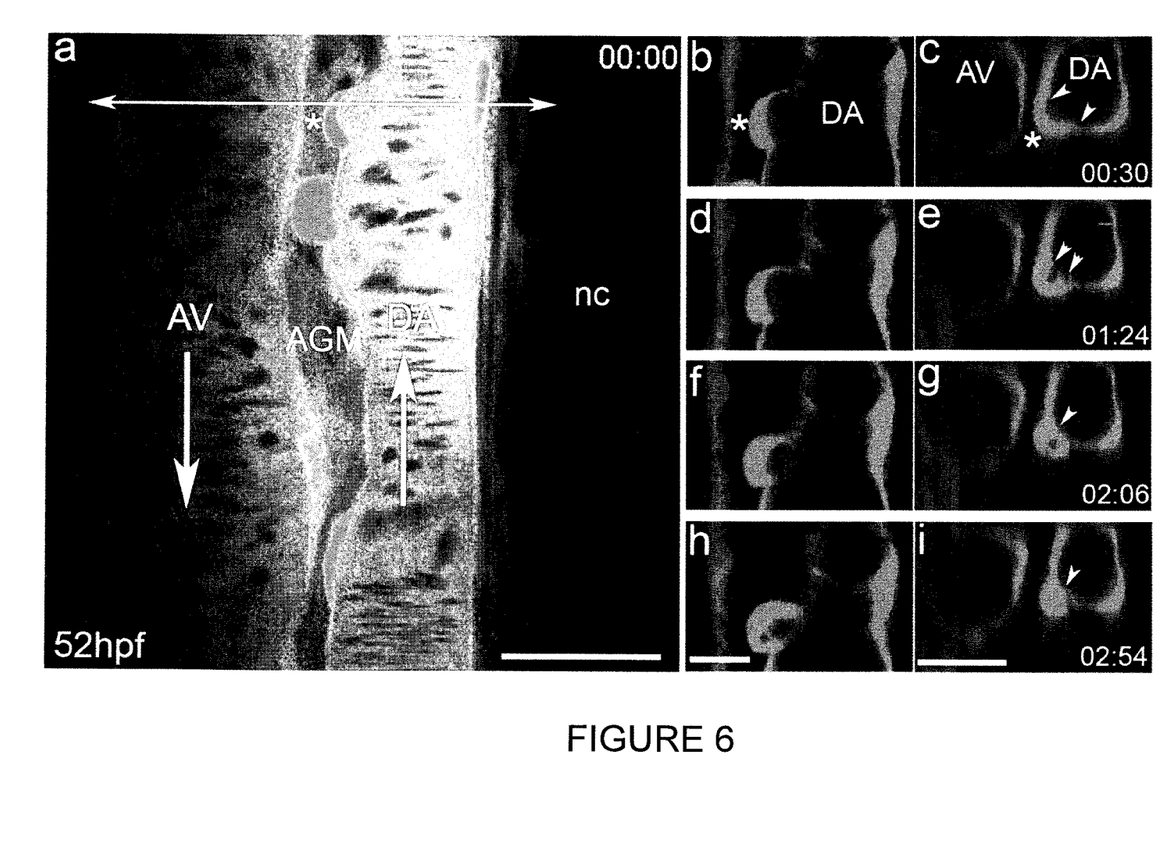
FIG. 6: Simultaneous longitudinal and transverse imaging of the exit and haematopoietic transformation of an endothelial cell from the aortic floor into the sub-aortic space.

Movie 2. This movie goes together with FIG. 6 and Movie 3. It shows in a KDR-GFP 2 d.p.f. embryo the exit and haematopoietic transformation of an endothelial DA floor cell (the topmost one) into the sub-aortic space, in sagittal view—the same cell being followed in transverse view in Movie 3. Another brightly GFP+ cell freshly escaped from the DA floor at the beginning of the movie, undergoes mitosis in a transverse plane, and one of the daughter cells swiftly joins the microstroma of the roof of the axial vein (to the left).

Movie 3. This movie shows in transverse view in a KDR-GFP 2 d.p.f. embryo the exit from the DA floor and haematopoietic transformation of the same endothelial cell followed in longitudinal view in Movie 2 (top) and FIG. 6. The times indicated in the upper right corner in Movies 2 and 3 match each other, allowing to compare the longitudinal and transverse views of the cell at each time point (1 frame/6 min.). The transverse optical sections were obtained by orthogonal projection of a stack of 73 confocal z-planes spaced by 0.6 µm.

Movie 4. This movie shows a 40 min. (1 frame/2 min.) time-lapse confocal imaging of a [KDR-GFP; Lmo2-Dsred] embryo in the AGM area. KDR-GFP+ haematopoietic cells born by EHT from the DA cells now evolve in the sub-aortic space and within the microstroma formed by the reticulation of the axial vein (AV) roof. Two of them, marked by asterisks in the first image, are seen entering the blood circulation. Due to the scanning process, red stripes reflect the trajectories of lmo2-dsred+ erythrocytes circulating in the DA and AV. Time is indicated in hours, minutes, seconds, in the upper right corner of the image. Each image is the maximum projection of three z-planes spaced by 1 µm.

Figure 3:
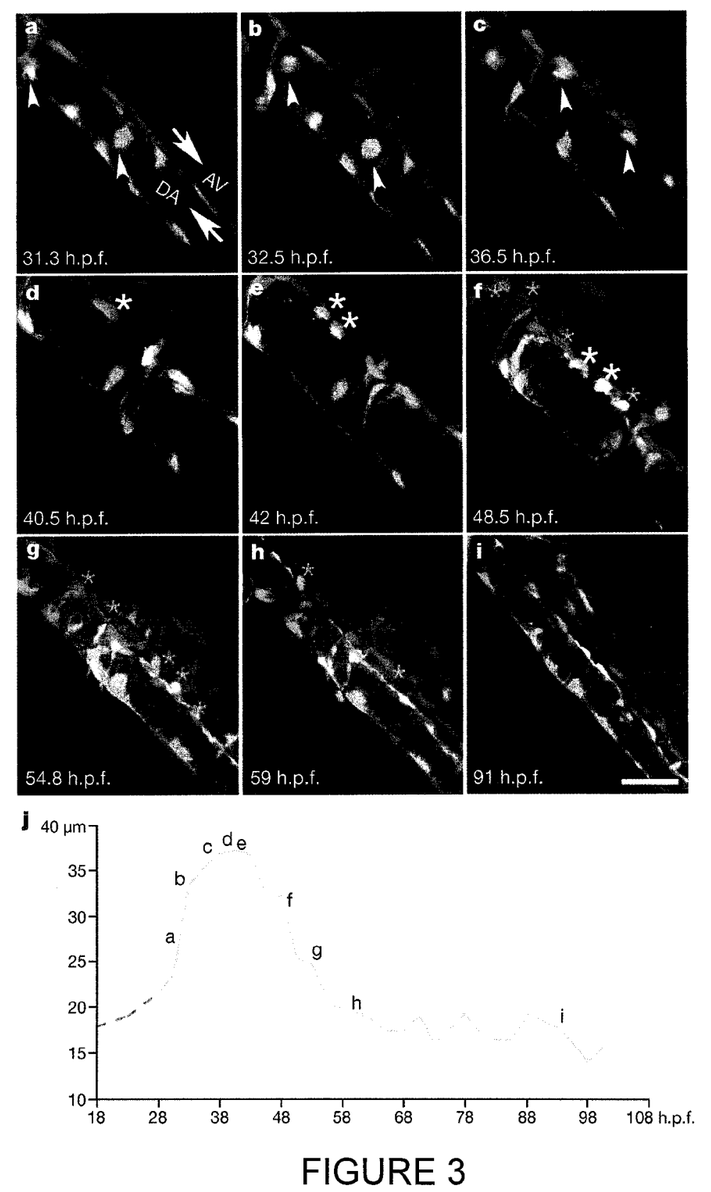
FIG. 3: The developmental phase of DA floor cells delamination (or EHT) and the transformation into HSPCs correlate with a phase of DA radial shrinking, preceded by a phase of DA radial expansion.

Movie 5. This movie shows the time-lapse confocal imaging of GFP fluorescence in a KDR-GFP embryo/larva from 28 h.p.f. to 100 h.p.f. (1 frame/5 min.). The first asterisks to appear point at two DA endothelial cells that migrate to the DA floor. The next ones point at DA floor cells undergoing EHT to become haematopoietic cells. The maximum projection from 18 z-planes spaced by 3 µm, is color-coded such that cells change colors as they move from one z-plane to another. Selected frames of this movie are shown in FIG. 3a-i. The movie was cut at 60 h.p.f. (after which no delamination occurred) to reduce file size; the remaining sequence from 60 to 100 h.p.f. is available upon request.

Movie 6. This movie shows the time-lapse confocal imaging of GFP fluorescence between 29 and 39 h.p.f. (1 frame/6 min.) in the AGM area of a KDR-GFP embryo in which runx1 expression was knocked-down by a morpholino. Numbers appear in the movie to point at DA floor cells that initiate EHT but then burst into pieces. Images are maximum projections from 22 z-planes spaced by 2 µm. Selected frames of this movie are also shown as FIG. 4.

The movies are also available in the inventors' reference 7.

DETAILED DESCRIPTION OF THE INVENTION

The present inventors have developed a new tool for studying endothelial-haematopoietic transition (EHT). In the context of the present invention, EHT and delamination are synonymous.

More particularly, the inventors have shown that some endothelial cells which make up the aorta undergo a strong bending outward, then fold upon themselves and round up to detach from the vascular wall, while still maintaining the integrity of the aorta. Each endothelial cell then becomes a free travelling stem cell.

Formation of haematopoietic stem cells (HSC) (mobile cell) in zebrafish occurs after transition of aortic endothelial cells (a type of epithelial cell) into haematopoietic stem cells (a type of mobile, migrating cell). This identical change is correlated with the lost of tight junctions between the endothelial cells.

The formation of HSC does not involve an asymmetric division, contrary to what is often the case in stem cell genesis.

The aortic endothelial cell having lost its tight junctions detaches from the vascular wall without affecting either the integrity or the permeability of the aorta.

This phenomenon is very similar to the EMT phenomenon (lost of tight junction and acquisition of migration property).

Accordingly, such a tool advantageously allows to study, in vivo, the events associated with EHT or EMT. A non exhaustive list of EHT or EMT-dependent events is the production of HSCs, and the mechanism of tumour metastasis and progression. The contemplated tool of the invention may be also used to observe the effect of elements (such as heat, irradiation, stress) on the mechanism of the EHT or EMT.

It is therefore an object of the invention to provide as a new tool, a fish embryo or larva, or a part thereof (such as the tail of the embryo or larva), which can be used as a model for the study of endothelial-haematopoietic transition (EHT) or epithelial-mesenchymal transition (EMT). As one skilled in the art may appreciate, the fish embryo or larva may be derived from a zebrafish or Medaka. In another particular embodiment, the contemplated fish embryo or larva of the invention comprises fluorescent vascular cells, such as arterial cells.

The contemplated fish embryo or larva of the invention may be advantageously a transgenic fish embryo or larva which expresses a reporter gene under regulatory sequences from a marker for vascular cells (e.g. arterial-specific cells) or HSC cells. Such a marker may be for instance a marker specific for haematopoietic precursors, a HSC marker. The marker is CD41, runx1 or cmyb[8], for instance.

In another aspect of the invention, the marker is an endothelial marker, known by the person skilled in the art, including but not limited to KDR (called flk1 in mammals), kdrl, Fli, Fli-1, Lmo2, ephrinB2, and Tie-2. The marker may be used as a non-toxic control, or a positive control together with a HSC marker providing two colors (e.g. green/red) in the caudal region once the EHT completed.

The advantage of having a fish embryo or larva with fluorescently labelled cells is to allow the study of the EHT or EMT-dependent events for example on embryo slices or in real time with any suitable methods known to one skilled in the art, such as non invasive fluorescence imaging (e.g. as described in the Example section).

The fluorescent cells may be obtained with any suitable dye known to one skilled in the art, or any other reporter gene[9]. For instance, the dye may be the green fluorescent protein (GFP) or the discosoma red protein (Dsred) expressed from the promoter of a vascular specific gene (e.g. KDR or Tie-2 or Fli-1 or Lmo2 gene), or of a gene expressed in HSCs (e.g. CD41, runx1 or cmyb). In this connection, the present invention contemplates of using transgenic embryos such as transgenic zebrafish embryos like those selected from the group consisting of CD41-GFP zebrafish, KDR-GFP zebrafish, Tie2-GFP, Fli-1-GFP, Lmo2-GFP, Lmo2-Dsred zebrafish and Lmo2-Dsred/CD41-GFP zebrafish.

As one skilled in the art may appreciate, the transgenic fish embryo or larva according to the present invention is used for the study of modulation (e.g. in vivo modulation) of EHT[9] and then EMT. One skilled in the art will understand that the modulation consists of inhibiting or inducing the EHT or EMT mechanism.

In this connection, another object of the invention is to provide a method for screening a candidate compound that modulates the endothelial-haematopoietic transition (EHT) or the epithelial-mesenchymal transition (EMT) mechanism. The method comprises the steps of:
  introducing a candidate compound into a fish embryo or larva as defined above and
  evaluating the capacity of said candidate compound to modulate the EHT mechanism.

This candidate compound is a DNA molecule, a RNA molecule, a protein, a virus, a chemical, a drug or any other suitable compound. The evaluation is made through screening, high-throughput screening, intravenous injection, or any other method known to the person skilled in the art.

The step of evaluating the capacity of the candidate compound to modulate the EHT or EMT mechanism may be achieved by observing the modulation, for instance, at the level of the aortic vessel of said fish embryo or larva or may be achieved by observing the amount of cells accumulated in the tail of the embryo or larva (e.g. in the caudal haematopoietic tissue).

As mentioned above, modulation of the EHT or EMT may be the inhibition or increase of the EHT or EMT activity.

As used herein, the terms "inhibit", "inhibition", "inhibitory", and "inhibitor" all refer to a function of reducing a biological activity or function associated with EHT or EMT.

As used herein, the term "increase in EHT or EMT activity" refers to an enhanced level of measurable EHT or EMT activity in a given assay, e.g. HSC emergence, in the presence of a candidate compound relative to the measurable level of EHT or EMT activity in the absence of a candidate compound.

EXAMPLE

Hematopoietic Stem Cells Emerge In Vivo from Aortic Endothelium by a New Type of Endothelial-Haematopoietic Transition Introduction Here the inventors show by non invasive, high-resolution imaging of live zebrafish embryos, that HSCs emerge directly from the aortic wall or floor, i.e. the embryo's main artery, through a stereotyped process that does not involve cell division but a strong bending then delamination or egress of single endothelial cells from the aortic ventral wall into the sub-aortic space, and their concomitant transformation into haematopoietic cells. The delamination process is polarized not only in the dorso-ventral but also in the rostro-caudal versus medio-lateral direction, and depends on runx1 expression: in runx1-deficient embryos, the delamination or exit events are initially similar, but much rarer, and abort into violent death of the delaminating or exiting cell. These results demonstrate that the aortic floor or ventral wall is haemogenic and that HSCs emerge from the endothelial wall of the aorta into the sub-aortic space, not by asymmetric cell division but through a new type of cell behaviour called endothelial-haematopoietic transition (EHT).

METHODS

Figure 2:
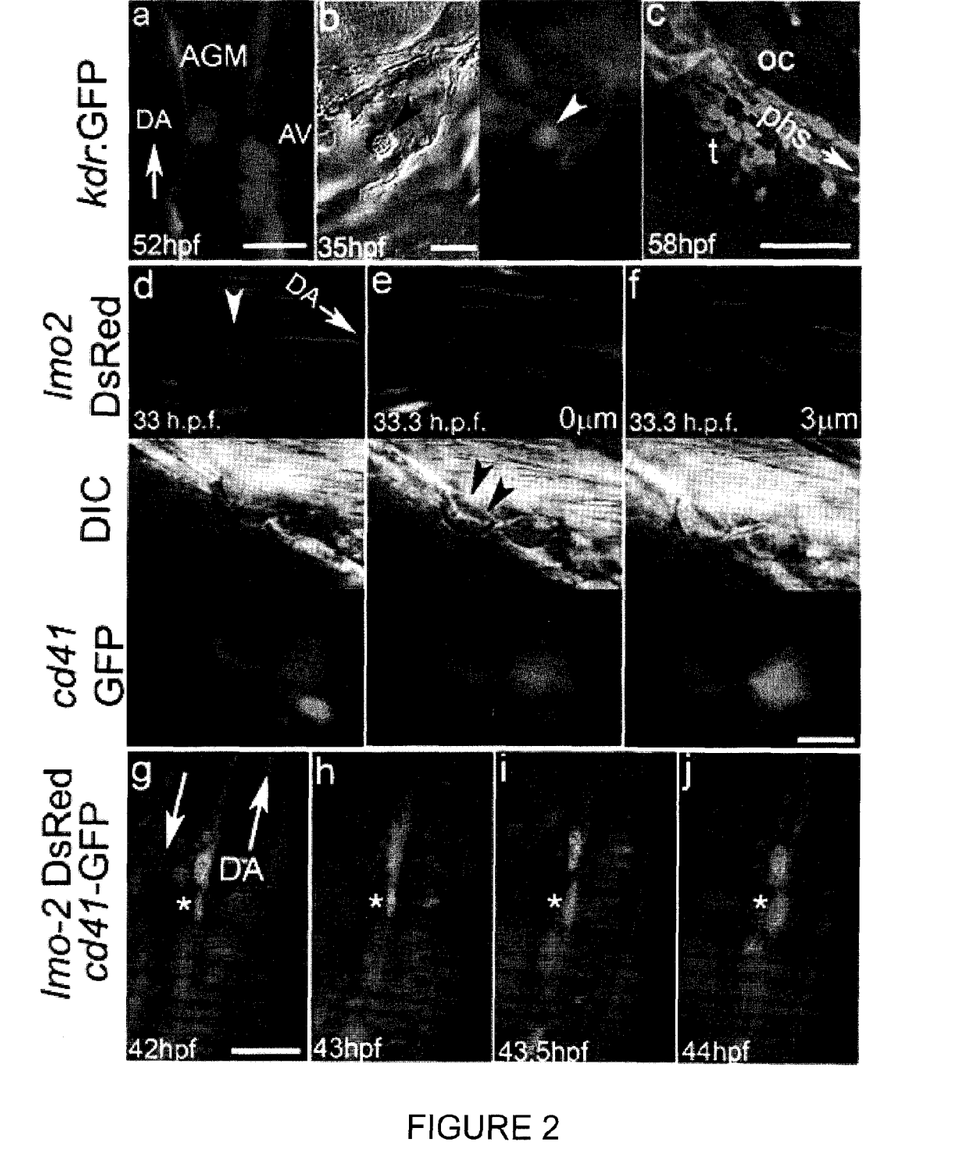
FIG. 2: The hematopoietic cells that emerge by delamination of aorta floor endothelial cells are HSPCs that seed the successive hematopoietic organs.

Zebrafish husbandry and embryo treatments. Zebrafish embryos were obtained from the Zebrafish International Resource Center at the University of Oregon and were raised and staged as described previously[10]. The KDR-GFP, Lmo2-Dsred and CD41-GFP transgenic lines used here have been described[11,12,13]. Runx1 morpholino mediated knock-down was performed as in a previous study[14] by the inventors. For the experiment shown in FIG. 2d-g, a plasmid bearing a KDR-dTomato reporter gene[15,16] and one I-SceI site was injected together with I-SceI meganuclease into CD41-GFP embryos at the I-cell stage, as described[17].

In vivo imaging. Embryos were anaesthetized and mounted for time-lapse confocal fluorescence microscopy as described previously[14]. Confocal microscopy was performed at 26° C. on two Leica SPE microscopes, one in upright configuration (FIG. 3 and Movies 2, 3, 5), the other in inverted configuration (FIGS. 1, 2, 4, 5 and Movies 1, 4, 6), with a 40× oil (FIG. 1b-v, FIG. 2a, d-f, FIG. 4 and FIG. 7h-j,), 16× oil (FIG. 2c, g-j, FIG. 7 k-n), or 20× water immersion (FIG. 3) objective. Maximum or color-coded projection of z-stacks, as well as red/green/DIC signal overlay, aortic diameter measurements, and export of time-lapse series as avi movies were performed with the Leica LAS software driving the confocal microscope. Avi movies were cropped and annotated with the ImageJ software, then compressed and converted into Quicktime movies with the Quicktime Pro software. Combined video-enhanced differential interference contrast (DIC) and fluorescence widefield imaging (FIGS. 1a and 2b) was performed on a Nikon 90i microscope as previously described[14].

Results and Discussion

The inventors[10,14] and others[18,19] have previously shown that in zebrafish embryos, the very thin space that initially separates the dorsal aortic (DA) from the underlying axial vein (AV) all along the trunk is the anatomical and functional homologue of the aorta-gonad-mesonephros (AGM) in mammals, that is, it contains the multipotent haematopoietic stem/progenitor cells (HSPCs) that will enter circulation to colonize, expand and differentiate in the subsequent haematopoietic organs, first the Caudal Hematopoietic Tissue (CHT)[10], which plays a haematopoietic role similar to the foetal liver in mammals, and then the definitive haematopoietic organs—the thymus and kidney marrow in fish.

In mammalian and avian ontogeny, CD41 has been the earliest marker distinguishing blood progenitors from endothelial cells/progenitors, notably in the AGM[5]. Accordingly, in transgenic CD41-GFP (green fluorescent protein) zebrafish embryos, the inventors reported that HSPCs can be first detected in the AGM of live zebrafish embryos as CD41-GFP$^{low}$ cells that appear asynchronously there from 33 hours post-fertilization (h.p.f.) until past 54 h.p.f.[14]. Each newly appeared CD41-GFP$^{low}$ cell then enters circulation through the underlying axial vein within the next 2-3 hours, to almost immediately seed the Caudal Hematopoietic Tissue (CHT), expand there, and later seed the thymus and kidney[14].

In the present work, the inventors investigated whether these HSPCs might arise from the aortic endothelium. The inventors took advantage of the KDR-GFP transgenic line, in which the promoter of the kdr1 gene[20] drives vascular-specific GFP expression from the angioblast stage[11], and the inventors followed up systematically the behaviour of aortic cells in live embryos by time-lapse fluorescence confocal microscopy, from the stage of aortic formation (18 h.p.f.) to 100 h.p.f. (well beyond the peak of HSPC generation in the AGM and seeding of the CHT). Starting from about 30 h.p.f., the imaging revealed a high frequency of endothelial cells from the aortic floor that underwent lasting contraction then bending towards the sub-aortic space, and remained in this strongly bent configuration for typically 1-2 hours (FIGS. 1d, e, k, FIGS. 2d 6 and 7h). Then a further contraction of the bent DA floor cell along the medio-lateral axis brought its two lateral (left and right) endothelial neighbours in contact with each other (FIG. 1f, l, FIG. 2e, arrowheads, FIG. 5, FIG. 7e, 7g, 7i, movie 3). The cell then released its contact with its now joined left and right neighbours, but still maintained strong focal contact with both its rostral and its caudal neighbours (FIG. 1g, h, m, n, 6), while rounding up and already manifesting motility, leading to its oscillatory motion along the vessel's axis (see for example cell #9 in FIG. 1m, n and Movie 1). Then these distal contacts also dissolved, and the now free cell started to move in the sub-aortic space, with a typical haematopoietic progenitor morphology (Movies 1 to 4). The successive steps that the inventors could discern in this stereotyped delamination sequence are recapitulated in FIG. 5. They reveal how an endothelial cell that is part of the vascular floor is able to delaminate from it without compromising the vessel's integrity. Each endothelial cell then becomes a "free travelling" stem cell which will divide so as to eventually give rise to all the different types of blood cells. The inventors call this new type of cell transition an endothelial haematopoietic transition or EHT.

In about half of the cases, the resulting haematopoietic cell underwent apparently symmetrical division within the next two hours (FIG. 1o, p-s and Movies 1 and 2), then it entered a "microstroma" made by the reticulation of the dorsal wall of the underlying axial vein (FIG. 1s, 1r-u, FIG. 2a, Movies 1, 2, 4 and data not shown), and from there entered the vein lumen and blood circulation (FIG. 1t-v, 1u-v and Movies 1 and 4), as the inventors had previously documented with CD41-GFP embryos[14].

In the twosomite long segment of the DA observed and analyzed in FIG. 1 and Movie 1, two pairs of cells (#1 to 4 in FIG. 1b) were already round and off the DA floor at the onset of the movie, and six were seen undergoing the entire delamination or EHT sequence during the recording session, that is, between 36 and 52 h.p.f. (cells #5 to 10), showing that most if not all cells forming the DA floor at 35 h.p.f. eventually delaminate or undergo EHT. Four different embryos similarly imaged over 10-16 hours in the same 32-56 h.p.f. period displayed a similar frequency of EHT events: 0.19, 0.25, 0.27 and 0.36 per somite per hour). As the AGM extends over about 12 somites in length (somites 6-17[10]), this would mean about 36 cells (an average of 3 cells undergoing EHT per AGM per hour) delaminating between 36 and 52 h.p.f., about half of which will divide before leaving, hence about 3.4-4.5 cells per hour entering the blood to seed the CHT—in very good agreement with the inventors estimations of CHT seeding rate by CD41-GFP$^{low}$ HSPCs from the AGM (2.5 and 5 cells/hour at 35 and 48 h.p.f., respectively[14]).

Consistently, the first haematopoietic HSPCs that seed the CHT by 35 h.p.f.[14], previously shown to originate from the AGM[14], are KDR-GFP+ (FIG. 2b). By 3 days pf, KDR-GFP+ cells then heavily colonize the thymus (FIG. 2c), just as the CD41-GFP$^{low}$ HSPCs did in a previous study[14] by the inventors, but KDR-GFP expression appears to stay longer than CD41-GFP, and still illuminates many thymocytes in the early thymus up by 6 d.p.f. (data not shown). It was not possible to directly image potential KDR-GFP+ HSPCs in the kidney by 5 d.p.f., due to the deep location of the tissue and very dense KDR-GFP+ vascular network there. We therefore injected in CD41-GFP embryos a plasmid-borne KDR-dTomato transgene, so as to obtain a mosaic expression of the KDR-dTomato transgene in vascular cells, and then searched for KDR-dTomato+ free cells in the kidney area. Most of those that we found did coincide with CD41-GFP+ HSPCs (FIG. 2d-g, arrowheads).

Figure 7:
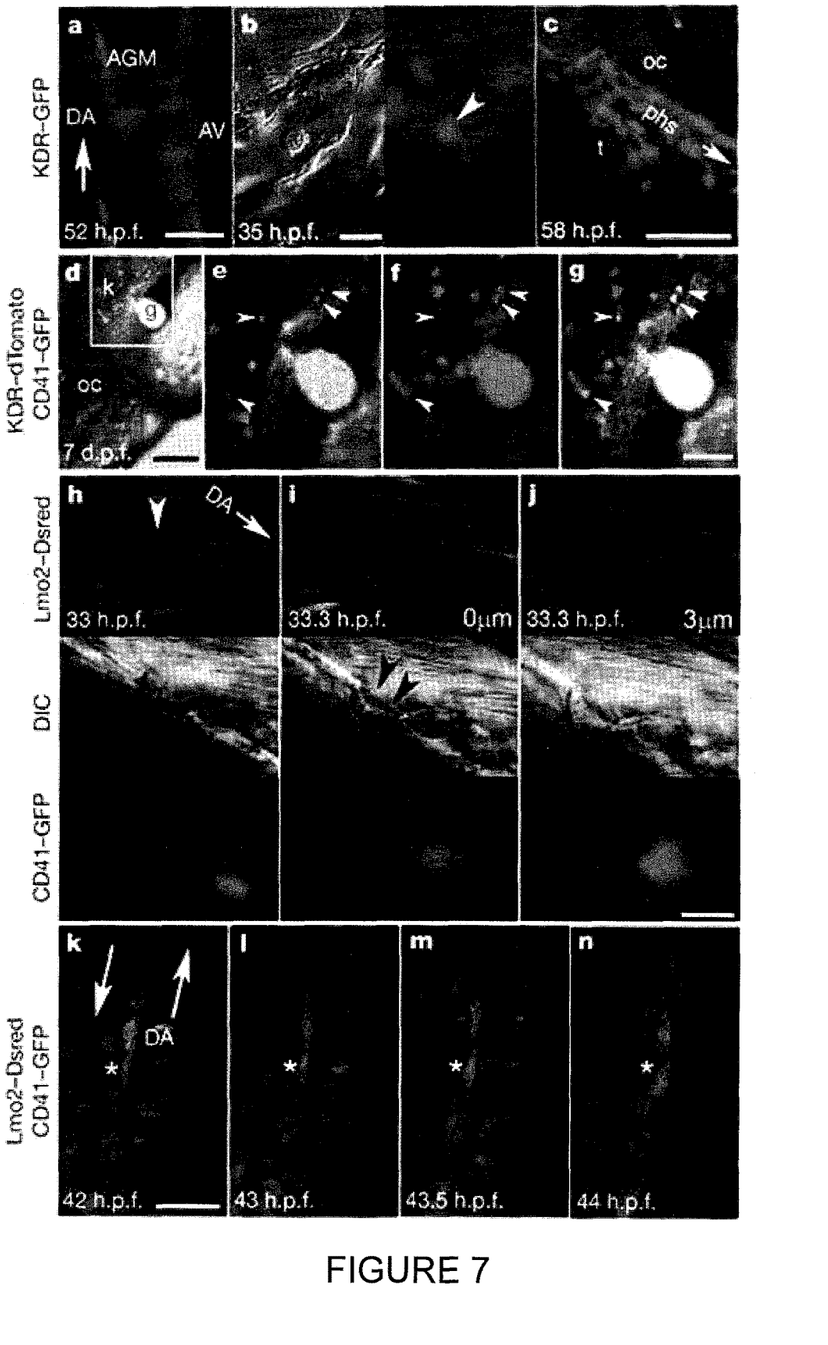
FIG. 7: The haematopoietic cells emerging by delamination (or EHT) of aortic floor endothelial cells are HSPCs that seed the successive haematopoietic organs.

To visualize the filiation between the aortic endothelial cells delaminating from the aorta, i.e. undergoing EHT and the initial emergence of CD41-GFP$^{low}$ HSPCs directly, the inventors used double transgenic [Lmo2-Dsred[12], CD41-GFP] embryos. Although Lmo2-Dsred expression in vascular cells is weaker than KDR-GFP, the inventors could detect the delamination (egress) of Lmo2-Dsred+ cells from the DA floor into the sub-aortic space, accompanied by the onset of detectable CD41-GFP expression, then a rise in the latter marking the resulting haematopoietic cells, as shown previously[14] (FIG. 2 d-j, 7h-n).

The inventors then addressed more closely the circumstances of the delamination or EHT events. The inventors first noticed a temporal correlation between these individual events and previously undescribed phases of the development and behaviour of the DA as a whole. FIG. 3 and Movie 5 show the evolution of the DA area in a single embryo followed from 23 to 100 h.p.f.

The inventors noted that between DA formation (at 18 h.p.f.) and 37 h.p.f., the DA diameter is steadily enlarging, from 18 to 37 µm, with a steep increase between 30 and 37 h.p.f. (FIG. 3a-d, j). During this period, DA endothelial cells undergo rearrangements relative to each other, some of which are quite extensive, bringing some endothelial cells from the lateral or even dorsal side of the DA, to the DA floor (FIG. 3a-c, arrowheads and Movie 5). Cells start delaminating (undergoing EHT) from the DA floor, then from 40 to 52 h.p.f., corresponding with the peak of delaminations (EHT events) (FIG. 3d-g and Movie 5) and CHT seeding[14], the diameter of the aortic now steadily decreases from 37 to 20 μm (FIG. 3j); then as delamination (EHT) events become rarer, the DA diameter decreases more slowly (from 20 to 17.3 μm between 52 h.p.f. and 65 h.p.f.; FIG. 3h-j). No more delaminations (EHT events) were detected in the AGM past 60 h.p.f. A similar DA evolution was observed in four different embryos, with DA width always peaking by 36-40 h.p.f. This temporal correlation between DA floor cell delamination and gradual reduction of DA diameter is likely meaningful. Indeed the delamination (EHT) process as the inventors understand it from the imaging involves the joining of the lateral (rather than rostral and caudal) neighbours of the delaminating cell (undergoing EHT), which by itself tends to reduce the vessel's diameter significantly (FIG. 6) from the DA circumference consists in no more than four cells. So the two processes, the delamination (egress) of DA floor cells, which if unaided, would likely involve considerable biomechanical forces locally, and the global shrinking of the vessel, which may involve a biomechanical effort more distributed among all DA cells, work in the same direction and may thus facilitate each other.

The process the inventors have shown here is a novel type of epithelial to mesenchymal transition (EMT)[21]; it concerns a squamous epithelium, the arterial endothelium, hence may be called an EndMT[22]. While the endothelial to haematopoietic transition, or EHT, described here is entirely novel, it bears some common features with the phenomenon of epithelial to mesenchymal transition (EMT), which is central to vertebrate development[21], and cancer. To the inventors' knowledge, only one physiological EndMT concerning a vascular endothelium had been described and analyzed so far: the formation of cardiac valves by transformation of endocardial cells into a mesenchymal cushion[23]. In this case however, a patch of contiguous squamous endothelial cells first turn into a columnar epithelium, before underlying classical EMT. In contrast, the EndMT described here affects individual cells, asynchronously, that turn directly from squamous endothelial into hematopoietic cells.

It seems to the inventors that the spectacular initial steps of the observed process, the strong bending of the endothelial cell towards the sub-aortic space, then the joining of its lateral neighbours, might be the biomechanical equivalent for a squamous epithelium of the apical constriction process described for columnar epithelia, notably that which initiates gastrulation in Drosophila to then give rise through an EMT to the mesoderm cells[24]. This apical constriction was recently shown to occur not gradually but by discrete contractions at the individual cell level followed by stabilization of the constricted steps[24], not unlike what the inventors have observed here.

While others have identified cells emerging in the lumen of the aorta, budding directly from ventral endothelial cell[9,25] the inventors have thus shown the mechanism of EHT, a process that does not include cell division.

Figure 4:
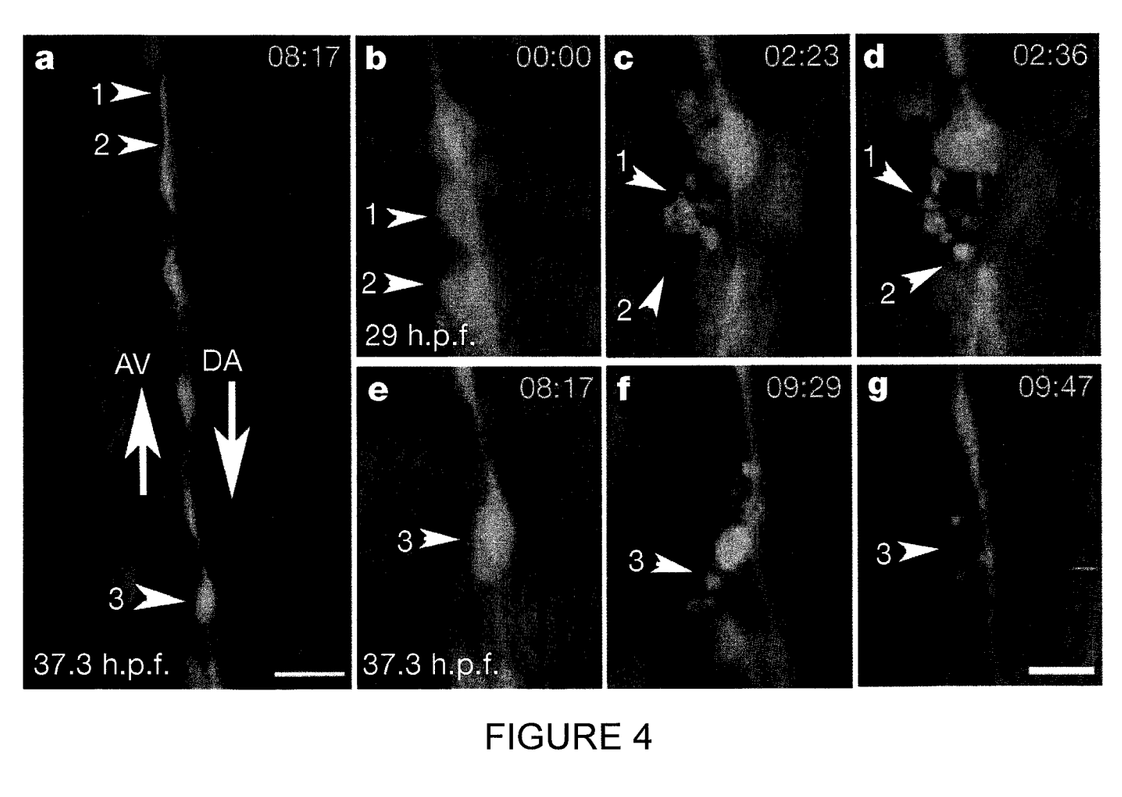
FIG. 4: Runx1 expression is required for the successful delamination (or EHT) and transformation of DA floor cells into HSPCs.

Finally, since the emergence of HSCs in the embryo of both amniotes and zebrafish is known to require the runx1 transcription factor[14,18,26,27], the inventors suppressed specifically its expression in the developing embryos with a morpholino, as the inventors did in their previous study[14]. The inventors found that in these runx1 morphants, once the DA is formed, its cells express the KDR-GFP transgene as in control embryos (FIG. 4a). Then from 32 h.p.f. onwards, some delamination (EHT) events are initiated, but much more rarely than in normal embryos, and they are abortive: the endothelial cell contracts, initiates EHT (EMT), but then bursts into pieces as it rounds up to become a haematopoietic cell (FIG. 4 b-g and Movie 6). Consequently, the CHT and then thymus are not seeded (Reference 14 and data not shown). On the basis of these data, the inventors propose that runx1 expression is required in the endothelial cell[26] to achieve the EHT (EndMT) successfully.

It is very likely that the EndMT (EHT) described here for the zebrafish will also apply to the AGM of mammals[6,28,29,30] and birds, and more generally to any haemogenic endothelium.

At a more general level, the EHT is a novel type of cell transition by which a cell that belongs to a squamous epithelium, the blood vessel, can leave it to become a free cell without compromising the vessel's integrity. Only one process of epithelial to free cell transition was known so far, the epithelial mesenchymal transition (EMT), which mostly concerns columnar epithelia, and is central to vertebrate development and cancer.

The experiments disclosed in the present application show that cells that are already specialized, such as those which make up a blood vessel, can naturally re-program themselves to become multipotent stem cells.

EXAMPLE

Example of Screening of Molecules

In every single well of a 96 wells plate, three embryos Cd41:GFP (screening of haematopoietic stem cells with a GFP reporter gene) of 25 h.p.f. are introduced.

The candidate compounds are introduced automatically. Each compound is added in the water tank and its effect is observed in the live embryo, in a non invasive way.

After 24 hours of incubation, the embryos are processed for imaging in their well, at 50 h.p.f.

From the generated pictures, quantification and comparison with control embryos are performed. Each compound is tested for its effect on EHT, is associated to a value between 0 and 100. 0 is for total inhibition of EHT. With a value above 100, the compound is selected for its inducing effect.

Toxicity of each candidate compounds on embryos development is also analysed.

REFERENCES

1 I. Godin and A. Cumano, *Nat Rev Immunol* 2 (8), 593 (2002).
2 M. Yoshimoto and M. C. Yoder, *Nature* 457 (7231), 801 (2009).
3 S. Taoudi and A. Medvinsky, *Proc Natl Acad Sci USA* 104 (22), 9399 (2007).
4 F. Dieterlen-Lievre, C. Pouget, K. Bollerot et al., *Trends in cardiovascular medicine* 16 (4), 128 (2006).
5 J. Y. Bertrand, S. Giroux, R. Golub et al., *Proc Natl Acad Sci USA* 102 (1), 134 (2005).
6 C. J. Marshall and A. J. Thrasher, *British Journal of Haematology,* 112, 838-850 (2001)
7 K. Kissa and P. Herbomel, *Nature,* 464 112-115, (2010) doi:10.1038/nature08761
8 North T. E. et al., *Nature,* 447, 1007, (2007) doi: 10.1038/nature05883
9 D. Baldessari and M. Mione, *Pharmacology & Therapeutics,* 118, 206-230 (2008)

10 E. Murayama, K. Kissa, A. Zapata et al., *Immunity* 25 (6), 963 (2006).
11 S. W. Jin, D. Beis, T. Mitchell et al., *Development* 132 (23), 5199 (2005).
12 H. Zhu, D. Traver, A. J. Davidson et al., *Dev Biol* 281 (2), 256 (2005).
13 H. F. Lin, D. Traver, H. Zhu et al., *Blood* 106 (12), 3803 (2005).
14 K. Kissa, E. Murayama, A. Zapata et al., *Blood* 111 (3), 1147 (2008).
15 N. C. Shaner, R. E. Campbell, P. A. Steinbach et al., *Nature biotechnology* 22 (12), 1567 (2004).
16 Y. Blum, H. G. Belting, E. Ellertsdottir et al., *Developmental biology* 316 (2), 312 (2008).
17 D. Soroldoni, B. M. Hogan, and A. C. Oates, *Methods in molecular biology* (Clifton, N.J. 546, 117 (2009).
18 M. Gering and R. Patient, *Dev Cell* 8 (3), 389 (2005).
19 H. Jin, J. Xu, and Z. Wen, *Blood* 109 (12), 5208 (2007).
20 J. Bussmann, N. Lawson, L. Zon et al., *PLoS Genet* 4 (5), e1000064 (2008).
21 E. D. Hay, *Dev Dyn* 233 (3), 706 (2005).
22 J. C. Kovacic and M. Boehm, *Stem Cell Res* 2 (1), 2 (2009).
23 D. Beis, T. Bartman, S. W. Jin et al., *Development* 132 (18), 4193 (2005).
24 A. C. Martin, M. Kaschube, and E. F. Wieschaus, *Nature* 457 (7228), 495 (2009).
25 Julien Y. Bertrand et al., *Nature,* 464, pp. 108-112 (2010) doi:10.1038/nature08738
26 M. J. Chen, T. Yokomizo, B. M. Zeigler et al., *Nature* 457 (7231), 887 (2009).
27 C. Lancrin, P. Sroczynska, C. Stephenson et al., *Nature* 457 (7231), 892 (2009).
28 Rachel David, *Nature Reviews, Molecular Cell Biology*, Vol. 11, 232-233 (2010) doi:10.1038/nrm2876
29 J-C. Boisset et al., *Nature,* 464, pp. 116-121, (2010) doi:10.1038/nature08764
30 H. M. Eilken, S. Nishikawa, and T. Schroeder, *Nature* 457 (7231), 896 (2009).

The invention claimed is:

1. A method of screening for a candidate compound that modulates the endothelial haematopoietic transition (EHT) mechanism, comprising the steps of:
   introducing candidate compound in a water tank containing a transgenic zebrafish embryo or larva, said transgenic zebrafish embryo or larva expressing a marker selected from the group consisting of CD41, runx1, cmyb, KDR, kdrl, Fli, Fli-1, Lmo2, ephrinB2 and Tie-2, and said marker being coupled to a reporter gene selected from the group consisting of green fluorescent protein (GFP) and discosoma red protein (Dsred), and
   detecting the apparition of fluorescent transgenic cells in the tail of the zebrafish embryo or larva to determine the capacity of said candidate compound to inhibit the transition of aortic endothelial cells into haematopoietic stem cells.

2. The method according to claim 1, wherein the transgenic zebrafish embryo or larva expresses the marker CD41 coupled to the reporter gene GFP.

* * * * *